US007666403B2

(12) United States Patent
Mayumi et al.

(10) Patent No.: US 7,666,403 B2
(45) Date of Patent: Feb. 23, 2010

(54) MUTANT INTERFERON α PROTEIN AND USE THEREOF

(75) Inventors: Tadanori Mayumi, Gurasuarina-Nishijin-Chuo 907, 1-1, Kojidai 5-chome, Nishi-ku, Kobe-shi, Hyogo (JP) 6512273; Yasuo Tsutsumi, 20-1,Shinkofudai 2-chome, Toyono-cho, Toyono-gun, Osaka (JP) 5630105; Shinsaku Nakagawa, 4-1, Nishikinomoto 4-chome, Yao-shi, Osaka (JP) 5810045; Madoka Taniai, Okayamai (JP); Kakuji Torigoe, Okayamai (JP); Masashi Kurimoto, Okayamai (JP)

(73) Assignees: Kabushiki Kaisha Hayashibara Seibutsu Kagaku Kenkyujo, Okayama (JP); Tadanori Mayumi, Hyogo (JP); Yasuo Tsutsumi, Osaka (JP); Shinsaku Nakagawa, Osaka (JP)

( * ) Notice: Subject to any disclaimer, the term of this patent is extended or adjusted under 35 U.S.C. 154(b) by 424 days.

(21) Appl. No.: 11/719,283

(22) PCT Filed: Nov. 9, 2005

(86) PCT No.: PCT/JP2005/020514

§ 371 (c)(1), (2), (4) Date: May 14, 2007

(87) PCT Pub. No.: WO2006/051805

PCT Pub. Date: May 18, 2006

(65) Prior Publication Data

US 2009/0311218 A1 Dec. 17, 2009

(30) Foreign Application Priority Data

Nov. 12, 2004 (JP) ............................ 2004-329461

(51) Int. Cl.
*C07K 14/52* (2006.01)
*C12N 15/21* (2006.01)
*A61K 38/21* (2006.01)

(52) U.S. Cl. .................. 424/85.7; 435/69.51; 530/351; 530/402; 424/85.4

(58) Field of Classification Search ...................... None
See application file for complete search history.

(56) References Cited

OTHER PUBLICATIONS

Extended European Search Report mailed Sep. 10, 2008.
Kallen, K.-J. et al., "New perspectives on the design of cytokines and growth factors", Trends in Biotechnology, Elsevier Publications, vol. 18, No. 11, pp. 455-461, Nov. 1, 2000.
L. C. Roisman et al., "Mutational Analysis of the IFNAR1 Binding Site on IFNa2 Reveals the Architecture of a Weak Ligand-Receptor Binding-Site", Journal of Molecular Biology, vol. 353, No. 2 pp. 271-281, Oct. 21, 2005.
H. Schooltink et al., "Designing Cytokine Variants by Phage-Display", Combinatorial Chemistry & High Throughput Screening, vol. 8, No. 2, pp. 173-179, Mar. 2005.
H. Renqui et al., "Protein Engineering of Interferon Alphas", Methods in Molecular Medicine, vol. 116, pp. 69-80, 2005.

*Primary Examiner*—Christine J Saoud
*Assistant Examiner*—Jegatheesan Seharaseyon
(74) *Attorney, Agent, or Firm*—Browdy and Neimark, PLLC

(57) ABSTRACT

The present invention has objects to provide a mutant interferon-α protein having a higher anti-viral and anti-tumor activity and to provide an agent for susceptive diseases, which contains the mutant interferon-α protein as an effective ingredient; and solves the above objects by providing a mutant protein which has an amino acid sequence of human interferon-α subtype α8 represented by any one of SEQ ID NOs:1 to 3, where the arginine residue at the $145^{th}$ has been replaced with leucine, isoleucine, or valine residue; the alanine residue at the $146^{th}$ has been replaced with asparagine or serine residue; and the methionine residue at the $149^{th}$ has been replaced with tyrosine residue; and an agent for susceptive diseases, containing the mutant protein.

6 Claims, No Drawings

MUTANT INTERFERON α PROTEIN AND USE THEREOF

TECHNICAL FIELD

The present invention relates to a novel mutant interferon-α protein, more particularly, to a mutant interferon-α subtype α8 and an agent for susceptive diseases, which contains the same.

BACKGROUND ART

In recent years, it was reported that human interferon-α (may be called "IFN-α", hereinafter) subtype α8 (may be simply called "IFN-α8", hereinafter) exhibits a superior activity to other IFN-α subtypes, accepted as pharmaceuticals, such as subtypes α2a and α2b (may be respectively called "IFN-α2a" and "IFN-α2b", hereinafter). For example, Foster G. R., Rodrigues O., Ghouze F., Schulte-Frohlinde E., Testa D., Liao M. J., Stark G. R., Leadbeater L., and Thomas H. C. reported in *Journal of Interferon & Cytokine Research*, Vol. 16, No. 12, pp. 1027-1033, 1996, that IFN-α8 shows an extremely higher anti-viral activity than other IFN-α subtypes. Yanai Y., Horie S., Yamamoto K., Yamauchi H., Ikegami H., Kurimoto M., and Kitamura T. reported in *Journal of Interferon & cytokine Research*, Vol. 21, No. 12, pp. 1129-1136, 2001, that IFN-α8 exhibits a superior anti-tumor activity on kidney cancer to other IFN-α subtypes.

The above reports show that IFN-α8 has a superior activity to other IFN-α subtypes, however, the fact was found based on the results only from in vitro experiments and the difference in activity between IFN-α8 and other IFN-α8 subtypes is not so distinct. Therefore, if only mutant IFN-α8 proteins having a much higher activity than conventional IFN-α preparations or IFN-α8 were obtained, they would expectedly expand the use of IFN-α.

DISCLOSURE OF THE INVENTION

In view of the foregoing, the present invention has an object to provide an agent for susceptive diseases, containing as an effective ingredient a mutant IFN-(protein having a superior anti-viral and anti-tumor activity to those of conventional IFN-αs.

The present inventors have eagerly studied and found that mutant IFN-α8 proteins having an amino acid sequence represented by any one of SEQ ID NOs: 1 to 3, where the arginine residue at the 145$^{th}$ has been replaced with isoleucine, leucine or valine residue; the alanine residue at the 146$^{th}$ has been replaced with asparagine or serine residue; and the methionine residue at the 149$^{th}$ has been replaced with tyrosine residue, are distinctly superior in activity to wild-type IFN-α8. They also found that lysine-replaced mutant IFN-α proteins, prepared by replacing one or more lysine residues in the amino acid sequence of the above mutant IFN-α proteins with other amino acid residue(s) can be conjugated with water-soluble polymers into physiologically active complexes having an extremely higher activity than other conventional IFN-α preparations conjugated with water-soluble polymers, and thus they accomplished this invention.

The present invention solves the above objects by providing mutant proteins having an amino acid sequence represented by any one of SEQ ID NOs: 1 to 3, where the arginine residue at the 145$^{th}$ has been replaced with leucine, a isoleucine or valine residue, the alanine residue at the 146$^{th}$ has been replaced with asparagine or serine residue, and the methionine residue at the 149$^{th}$ has been replaced with tyrosine; and an agent for susceptive diseases, which contains the mutant protein(s) as an effective ingredient.

BEST MODE FOR CARRYING OUT THE INVENTION

The mutant IFN-α proteins used in the present invention are those which have an improved IFN-α activity by replacing one or more amino acid residues in either of wild-type IFN-α8, particularly, IFN-α8a (SEQ ID NO:1), IFN-α8b (SEQ ID NO:2) or IFN-α8c (SEQ ID NO:3) with other amino acid residue(s). The mutant IFN-α proteins used in the present invention can be produced by usual gene technology. For example, to replace an objective amino acid residue(s) in the amino acid sequence of IFN-α8 with a random amino acid residue(s), a library, that expresses mutant proteins where the desired amino acid residues are replaced with a random amino acid residue(s), is obtained by applying NNS sequences to amino acid codons in the DNA encoding the amino acid sequence of IFN-α8 using techniques such as conventional oligo DNA synthesis, PCR technique, and DNA ligation technique. The library is applied to phage display method to express proteins, followed by screening the expressed proteins in combination with panning method using an antibody specific to IFN-α or its receptor protein, enzyme immunoassay, bioassay, etc., to obtain mutant IFN-α proteins with an improved IFN-α activity than IFN-α8. The phage display method is a quite useful technique for screening mutant IFN-α proteins because it exhaustively screens candidates for such mutant proteins.

The mutant IFN-α proteins used in the present invention are the ones prepared based on the report of Piehler J. (*The Journal of Biological Chemistry*, Vol. 275, No. 51, pp. 40425-40433, 2000) in such a manner of converting the amino acid residues in the amino acid sequence of IFN-α8, which had been recognized as being correlated to the binding with IFN-α receptor type 2, i.e., the amino acid residues at the 30$^{th}$, 33$^{rd}$, 145$^{th}$, 146$^{th}$, 149$^{th}$ and 150$^{th}$ in the amino acid sequence of IFN-α8, into random amino acid residues; exhaustively constructing mutant proteins by the above gene technology; and screening the desired mutant proteins having an amino acid sequence of IFN-α8 where, among the above amino acid residues, the arginine residue at the 145$^{th}$ has been replaced with isoleucine, leucine or valine residue; the alanine residue at the 146$^{th}$ has been replaced with asparagine or serine residue, and the methionine residue at the 149th has been replaced with tyrosine residue. The mutant IFN-α proteins with replacement of the above-identified amino acid residues at the 145$^{th}$, 146$^{th}$ and 149$^{th}$ have a remarkably improved activity. Thus, they are advantageously used as the mutant IFN-α proteins of the present invention.

Since IFN-α preparations have a poor stability in living bodies as mentioned above, they may be advantageously administered to such living bodies after formed into physiologically active complexes by allowing to conjugate with water-soluble polymers. However, IFN-α may possibly have a conjunct site that may lose its activity due to steric hindrance when conjugating with water-soluble polymers. Therefore, any mutant IFN-α proteins, whose conjunct sites with water-soluble polymers are restricted to specific sites free of causing activity loss, can be advantageously used in the present invention. Concretely explaining, when employing a method to conjugate water-soluble polymers with free amino groups of proteins, the conjunct sites in such proteins with the water-soluble polymers can be selected from the N-terminal or lysine residues. Mutant proteins, where one or more lysine residues have been replaced with other amino acid residue(s) (such mutant proteins are called "lysine-replaced mutant proteins", hereinafter), may possibly restrict proper conjunct sites for water-soluble polymers. Referring to the mutant IFN-α proteins of the present invention, the above-identified lysine residues at the $31^{st}$, $46^{th}$, $50^{th}$, $71^{st}$, $122^{nd}$, $134^{th}$, $135^{th}$, $160^{th}$, $163^{rd}$ and $165^{th}$ are replaced with random amino acid residues and screened for desired lysine-replaced mutant proteins, which retain the IFN-α activity and are suitable for conjugation with water-soluble polymers, by the above-mentioned gene technology. The present inventors found that at least one lysine residue should be remained intact in the lysine-replaced mutant proteins because mutant proteins, where all lysine residues have been replaced with other amino acids, result in an extremely reduced binding efficiency with water-soluble polymers; the lysine residue, that should be remained intact, is any one of the lysine residues at the $31^{st}$ and $134^{th}$. Therefore, the lysine-replaced mutant proteins of the present invention should preferably be prepared by retaining either of the lysine residues at $31^{st}$ and $134^{th}$ and replacing all the remaining lysine residues with other amino acid residues. The lysine-replaced mutant proteins thus obtained can be advantageously used in the present invention without losing their activity even when conjugated with water-soluble polymers. Examples of the mutant IFN-α proteins used in the present invention include those which have any one of the amino acid sequences of SEQ ID NOs:4 to 9 corresponding to the nucleotide sequences of SEQ ID NOs:10 to 15, respectively. These are shown in Table 1: "MUT1" is a mutant protein having an amino acid sequence of IFN-α8b, where the arginine residue at the $145^{th}$ in the amino acid sequence of IFN-α8 has been replaced with leucine residue, the alanine residue at the $146^{th}$ has been replaced with asparagine residue, and the methionlne residue at the $149^{th}$ has been replaced with tyrosine residue; "MUT2" is a mutant protein having an amino acid sequence of IFN-α8b, where the arginine residue at the $145^{th}$ in the amino acid sequence of IFN-α8 has been replaced with isoleucine residue, the alanine residue at the $146^{th}$ has been replaced with serine residue, and the methionine residue at the $149^{th}$ has been replaced with tyrosine residue; "MUT3" is a mutant protein having an amino acid sequence of IFN-α8b, where the arginine residue at the $145^{th}$ in the amino acid sequence of IFN-α8 has been replaced with leucine residue, the alanine residue at the $146^{th}$ has been replaced with serine residue, and the methionine residue at the $149^{th}$ has been replaced with tyrosine residue; and "MUT5" is a mutant protein having an amino acid sequence of IFN-α8b, where the arginine residue at the $145^{th}$ in the amino acid sequence of IFN-α8 has been replaced with valine residue, the alanine residue at the $146^{th}$ has been replaced with asparagine residue, and the methionine residue at the $149^{th}$ has been replaced with tyrosine residue. "MUT2K31" is a lysine-replaced mutant protein having an amino acid sequence of "MUT2", where all the lysine residues except for the one at the $31^{st}$ have been replaced with other amino acid residues; and "MUT2K134" is a lysine-replaced mutant protein having an amino acid sequence of "MUT2", where all the lysine residues except for the one at the $134^{th}$ have been replaced with other amino acid residues.

TABLE 1

| | Amino acid number | | | | | | | | | | | | | Note |
|---|---|---|---|---|---|---|---|---|---|---|---|---|---|---|
| | 31 | 46 | 50 | 71 | 122 | 134 | 135 | 145 | 146 | 149 | 160 | 163 | 165 | |
| IFN-α8b (Wild type) | K | K | K | K | K | K | K | R | A | M | K | K | K | SEQ ID NO:2 |
| MUT1 | K | K | K | K | K | K | K | L | N | Y | K | K | K | SEQ ID NO:4 (The present invention) |
| MUT2 | K | K | K | K | K | K | K | I | S | Y | K | K | K | SEQ ID NO:5 (The present invention) |
| MUT3 | K | K | K | K | K | K | K | L | S | Y | K | K | K | SEQ ID NO:6 (The present invention) |
| MUT4 | K | K | K | K | K | K | K | V | N | Y | K | K | K | SEQ ID NO:7 (The present invention) |
| MUT2K31 | K | G | R | G | R | H | T | I | S | Y | G | L | P | SEQ ID NO:8 (The present invention) |
| MUT2K134 | A | H | N | V | R | K | D | I | S | Y | R | A | T | SEQ ID NO:9 (The present invention) |

The mutant IFN-α proteins of the present invention can be obtained in a desired amount by introducing any one of the DNAs thus obtained, optionally after amplified, into a host such as *E. coli* with a plasmid vector for transformation and screening clones capable of producing desired proteins from the resulting transformants. Conventional methods for purifying proteins such as dialysis, salting out, filtration, concentration, centrifuging, separatory sedimentation, gel filtration chromatography, ion-exchange chromatography, hydrophobic chromatography, affinity chromatography, chromatofocusing, gel electrophoresis, and isoelectric focusing can be employed to collect the desired proteins from the cultures of transformants, which can be used in combination, if necessary. The mutant IFN-α proteins of the present invention have a specific activity of $2.5\times10^8$ IU/mg protein or more, preferably, $3\times10^8$ IU/mg protein or more, more preferably, $3.5\times10^8$ IU/mg protein or more, when assayed by applying a usual bioassay system using FL cells and sindbis virus. Since a bioassay using human colon cancer LS174T cells and vesicular stomatitis virus (VSV) detects IFN-α8 and mutant proteins thereof at a higher sensitivity, it can be advantageously used for evaluating the activity of the mutant IFN-α proteins of the present invention. In the case of calculating the specific activity of the mutant IFN-α proteins by the latter bioassay, they have a specific activities of, usually, $5\times10^8$ IU/mg protein or more, preferably, $1\times10^9$ IU/mg protein or more, and more preferably, $6\times10^9$ IU/mg protein or more.

Preferable water-soluble polymers used to artificially conjugate with the mutant IFN-α proteins of the present invention include those which are substantially water soluble ones, more particularly, those which are non-proteinaceous ones being neither harmful nor substantially antigenic to living bodies. Examples of such are synthetic polymers such as monopolymers including polyvinyl alcohol, polyethylene glycol, polyvinyl pyrrolidone, and polypropylene glycol; copolymers of ethylene glycol with vinyl alcohol or propylene glycol, and derivatives thereof; and natural polymers such as elsinan, dextran, hydroxyethyl cellulose, pullulan, and methyl cellulose. Among which, monopolymers of polyethylene glycol, copolymers of polyethylene glycol with other water-soluble polymers, and derivatives thereof are preferably used because they are easily obtained in the form of a uniform molecular weight. The molecular weight of the water-soluble polymers can be increased or decreased in the range of, usually, 500 to 200,000 daltons, preferably, 1,000 to 80,000 daltons. When the water-soluble polymers have a nonuniform molecular weight, they can be fractionated by usual methods such as separatory sedimentation and gel filtration chromatography before subjected to conjugation reaction with proteins. Varying depending on the kind of water-soluble polymers and the final use of the mutant IFN-α proteins, when the molecular weight of the water-soluble polymers is below the above range, the resulting complexes may become poor in dynamics in living bodies. While, when the molecular weight of the water-soluble polymers is over the above range, the complexes may become so poor in physiological activity as to lose their functions as pharmaceuticals.

To conjugate mutant IFN-α proteins with water-soluble polymers, the mutant IFN-α proteins are either reacted with water-soluble polymers pre-activated with agents capable of forming covalent bonds by specifically reacting with free amino groups, or bridged with water-soluble polymers using polyfunctional agents having active groups capable of specifically reacting with free amino groups. Such reactions can be carried out in accordance with the method disclosed in International Patent Publication No. WO95/13090. Methods commonly used in the art such as ester-conjugating method and amide-conjugating method, disclosed in Japanese Patent Kokai No. 289522/87, can be used. A preferable bond formed between a proteinaceous part and a water-soluble polymer is the one made by the amide conjugation method that forms a stable covalent bond.

Varying depending on the reaction method used, the ratio of a protein to a water-soluble polymer employed in the initiation reaction is increased or decreased within the range of 1:0.1 to 1:100, preferably, 1:0.5 to 1:50, and more preferably, 1:1 to 1:10 by molar ratio. In general, when the ratio is below the above range, the conjugation reaction efficiency lowers; while when the ratio is over the above range, the control of molecular number of water-soluble polymers conjugated with proteins becomes difficult. In any case, since the above conditions outside the above-identified range will lower the purification efficiency of the resulting physiologically active complexes, the ratio should usually preferably be increased or decreased within the above range. The reaction temperature, pH, and time are set so as not to inactivate and decompose the mutant IFN-α proteins and set to minimize undesirable side reactions: The reaction temperature is set to 0 to 100° C., preferably, 4 to 40° C.; the reaction pH is set to 0.1 to 12, preferably, 5 to 10; and the time is set to those which terminate the reaction within 0.1 to 50 hours, preferably, within 10 hours. The physiologically active complexes thus obtained can be purified by similar methods as used in purifying the mutant IFN-α proteins, and optionally further treated with concentration, salting out, centrifugation, lyophilization, etc., into products in a liquid or solid form, depending on final use.

The number of water-soluble polymers to be conjugated with one molecule of each of the mutant IFN-α proteins is usually at least one molecule, preferably, one or two molecules, more preferably, one molecule. The physiologically active complexes of the mutant IFN-α proteins of the present invention have a specific activity of $3\times10^6$ IU/mg protein or more, preferably, $1\times10^7$ IU/mg protein or more, and more preferably, $2\times10^7$ IU/mg protein or more, when assayed on a system of FL cells and sindbis virus; and have a specific activity of, usually, $2\times10^7$ IU/mg protein or more, preferably, $4\times10^7$ IU/mg or more, when assayed on a system of LS174T cells, derived from human colon cancer, and VSV.

The mutant IFN-α proteins or the physiologically active complexes thereof conjugated with water-soluble polymers according to the present invention are distinctly useful as agents for susceptive diseases for treating or preventing such diseases. The term "susceptive diseases" as referred to as in the present invention means diseases in general which can be treated or prevented by the administration of the agents of the present invention alone or in combination with other medicament(s). Examples of such diseases are solid tumors such as colon cancer, rectal cancer, gastric cancer, renal cancer, thyroid carcinoma, tongue cancer, bladder carcinoma, choriocarcinoma, hepatoma, carcinoma uteri, cancer of pharynx, lung cancer, breast cancer, malignant melanoma, neuroblastoma, pyo-ovarium, testicular tumor, osteosarcoma, pancreatic cancer, hypernephroma, goiter, brain tumor, malignant melanoma, and mycosis fungoides; hematopoietic tumors such as leukemia and lymphoma; viral diseases such as hepatitis B, hepatitis C, acquired immune deficiency syndrome (AIDS), and severe acute respiratory syndrome (SARS); bacterial diseases such as Chlamydia; and immune diseases such as allergic diseases and rheumatism. Thus, the agents for susceptive diseases of the present invention have a variety of uses as pharmaceuticals for treating/preventing the above diseases such as an anti-tumor drug, anti-viral drug, anti-bacterial drug, and drug for immune diseases.

Varying depending on the types and the symptoms of susceptive diseases to be applied, the agents for susceptive diseases of the present invention can be prepared to meet administration of at least 0.25 ng/kg body weight per dose, preferably, 2.5 ng to 400 μg/kg body weight per dose, depending on the administration route; and it can be prepared into those in the form of an extract, elixir, lower airway inhalation, capsule, granule, ophthalmic sustained-release drug, pill, ophthalmic ointment, cataplasm for tunica mucosa oris, suspension, emulsion, plaster, suppository, powder, tablet, syrup, dipping agent, decoction, injection, tincture, eye-drop, eardrop, nasal drop, troche, ointment, cataplasm, aromatic water, nasal nebulas, liniment, limonade, fluidextract, lotion, etc.

The agents for susceptive diseases of the present invention include those in a dose unit form containing, for example, any one of the agents in an amount equal to a single dose or an integral multiple dose (up to four times) of the single dose, or to a division of the single dose (up to 1/40 time); and those in the form of a physically separated systematic agent suitable for dosing. Examples of such agents include capsules, granules, pills, suppositories, powders, tablets, injections, and cataplasms.

The agents for susceptive diseases of the present invention mean those which contain, as an effective ingredient, the mutant IFN-α proteins and/or the physiologically active complexes thereof conjugated with water-soluble polymers according to the present invention. The agents can be used in combination with a wild-type IFN-α containing IFN-α8. Also, appropriate preparation agents such as excipients, ointment bases, dissolving agents, corrigents, odor masking or flavor imparting agents, colors, and emulsifiers, which are commonly used in preparing medicaments, can be freely incorporated into the agents for susceptive diseases of the present invention. Within the scope of the object of the present invention, the agents can be incorporated with one or more other medicaments, for example, external dermal agents such as external dermal sterilizing and pasteurizing agents, wound protecting agents, and antiphlogistics; vitamin preparations such as vitamin A preparations, vitamin B preparations, vitamin C preparations, vitamin D preparations, vitamin E preparations, and vitamin K preparations; revitalizers such as calcium preparations, mineral preparation, saccharide preparations, organic acid preparations, protein and amino acid preparations, and organ preparations; cell activating preparations such as chlorophyll preparations, and dye preparations; anti-tumor agents such as alkylating agents, antimetabolites, anti-tumor antibiotics preparations, and anti-tumor plant-ingredient preparations; allergic agents such as antihistamines; chemotherapeutics such as antituberculosis drugs, synthetic antimicrobial agents, and anti-viral agents; and others such as hormone preparations, antibiotic preparations, and biological preparations.

The agents for susceptive diseases of the present invention can be used in combination with the following as adjuvants; actinomycin D, aceglatone, ifosfamido, tbenimex, etoposide, enocitabin, aclarubicin hydrochloride, idarubicin hydrochloride, irinotecan hydrochloride, epirubicin hydrochloride, gemcitabine hydrochloride, daunorubicin hydrochloride, doxorubicin hydrochloride, nitrogen mustard-N-oxide hydrochloride, nimustine hydrochloride, pirarubicin hydrochloride, fadrozole hydrochloride hydrate, bleomycin hydrochloride, procarbazine hydrochloride, mitoxantrone hydrochloride, carboquone, carboplatin, carmofur, tamoxifen citrate, toremifene citrate, krestin, medroxyprogesterone acetate, cyclophosphamide, cisplatin, schizophyllan, cytarabine, cytarabine ocphosphate, zinostantin stimalamer, vinonelbin ditartrate, sobuzoxane, dacarbazine, thiotepa, tegafur, tegafur uracil, tegafur gimesutat otastat potassium, doxifluridine, docetaxel hydrate, toretinoin, neocarzinostatin, nedapiatin, paclitaxel, bicalutamido, picibanyl, hydroxycarbamide, busulfan, fluorouracil, flutamido, pentostatin, porfimer sodium, mitomycin C, mitobronitol, methotrexate, mercaptopurine, 6-mercaptopurine riboside, bleomycin sulfate, vincristine sulfate, vindesine sulfate, vinblastine sulfate, peplomycin sulfate, and lentinan. In the case of functioning the mutant IFN-α proteins also as immunoadjuvants, the combination use thereof may exert a quite high synergistic effect that could not be attained only with their single use. Such combination use would decrease the dose of anti-tumor drugs and this would remarkably reduce the side effects of the anti-tumor drugs as a merit.

The agents for susceptive diseases of the present invention exert therapeutic/prophylactic effects on susceptive diseases independently of their oral or parenteral administration routes. Depending on the types or the symptoms of susceptive diseases to be treated, the agents containing the mutant IFN-α protein(s) of the present invention are administered orally or parenterally through intradermal, subcutaneous, intramuscular, intravenous, intranasal, rectal, and intraperitoneal routes to a patient at a dose of 0.01 to 1,000 μg/day/kg body weight, preferably, 0.1 to 100 μg/day/kg body weight of each agent, where the dose is optionally divided into several portions and the administration frequency is one to seven doses per week for one week to one year, while observing the symptoms of the patient and the progress after the administration. Since the complexes of the mutant IFN-α proteins of the present invention, which are prepared by conjugating the proteins with water-soluble polymers, are stable, hardly decomposed by protease in the blood, and retained in living bodies for a significantly longer period of time than wild-type IFN-α8 by ten times or more depending on their administration route, the dose can be significantly minimized when administered to patients suffering from the same susceptive disease as those administered with the wild-type IFN-α8 by the same administration route. As a result, the complexes advantageously minimize side-effects induced by cytotoxicity to normal cells.

The following Experiments explain the preferred embodiments according to the present invention:

Experiment 1

Obtention of Mutant IFN-α Proteins

Experiment 1-1

Preparation of Phage Library

To obtain mutant IFN-α proteins with an improved IFN-α activity, the amino acid residues at the $30^{th}$, $33^{rd}$, $145^{th}$, $146^{th}$, $149^{th}$ and $150^{th}$ in the amino acid sequence of IFN-α8b (SEQ ID NO:2) were replaced with other amino acid residues. A chromosomal DNA was collected in usual manner from a human lyilphoblast cell line, BALL-1 cell (JCRB0071: Japanese Collection of Research Bioresources), and subjected to conventional PCR method using as primers oligonucleotides represented by SEQ ID NO:16 (having a restriction site of restriction enzyme NdeI, a start codon, and a nucleotide sequence at around the 5' terminus of IFN-α8) and SEQ ID NO:17 (having a restriction site of restriction enzyme BamHI, a stop codon, and a nucleotide sequence at around the 3' terminus of IFN-α8) to amplify a DNA specific to the primer sequences. The resulting amplified DNA was digested with restriction enzymes NdeI and BamHI. The resultant was introduced into a plasmid vector having T7 promoter region, T7 terminator region, ampicillin resistant region, and ColE1 •Ori region ("pET-3a", a product name of and commercialized by EMD Bioscience Corporation, USA) at the sites of the above restriction enzymes. The DNA region encoding IFN-α8 was analyzed by conventional DNA sequencer and revealed to have the nucleotide sequence of SEQ ID NO:18, a DNA encoding IFN-α8b. Using the revealed DNA as a template, it was subjected to PCR in usual manner with SEQ ID NO:19 (a primer for converting codons for the amino acids at the $30^{th}$ and $33^{rd}$ into NNS) and SEQ ID NO:20 (a primer for converting codons for the amino acid residues at the $145^{th}$, $146^{th}$, $149^{th}$ and $150^{th}$ into NNS), and the resulting PCR product as a template was subjected to PCR in usual manner with SEQ ID NO:21 (a primer for adding a cleavage site of restriction enzyme NcoI to the side of the 5-terminus) and SEQ ID NO:22 (a primer for adding a cleavage site of restriction enzyme NcoI to the side of the 3'-terminus). Thus, it was obtained a DNA represented by SEQ ID NO:23 having an amino acid sequence of IFN-α8, where the condons for the amino acid residues at the $30^{th}$, $33^{rd}$, $145^{th}$, $146^{th}$, $149^{th}$ and $150^{th}$ had been converted into random codons. The DNA thus obtained was digested with restriction enzymes NcoI and NotI and then incorporated into pCA NTAB 5E, a phagemid vector pre-digested with restriction enzymes NcoI and NotI, commercialized by Amersham Biosciences, Tokyo, Japan, by ligation reaction in usual manner. The incorporated DNA was introduced into a strain of *E. Coli*, TG-1, by conventional electroporation, and the resulting microorganism was cultured in 2YT medium containing 2% (w/v) glucose and 100 μg/ml of ampicillin, followed by adding to the culture $1\times10^9$ pfu/ml of M13K07, a helper phage, commercialized by Invitrogen Japan K.K., Tokyo, Japan, culturing the microorganism at 37° C. for one hour under shaking conditions, centrifuging the resulting culture to collect the precipitate, suspending the precipitate in 2YT medium containing 50 μg/ml of kanamycin and 100 μg/ml of ampicillin, and culturing the resulting microorganism at 37° C. for six hours. The resulting culture was centrifuged to obtain a supernatant containing the phage, followed by collecting the phage for a phage library by conventional sedimentation with polyethylene glycol.

Experiment 1-2

Selection of Phage Clone by Panning Method using IFN-α Receptor Type 2 (IFNAR2)

A fusion protein (SEQ ID NO:24), composed of extracellular domain of IFNAR2 isoform (SWISS-PLOT No. P48551) and Fc region of human immunoglobulin G, was prepared in usual manner by transient expression system using cultured animal cells, and fixed to "MAXI SORP", a product name of a polystylene immunotube commercialized by Nalge Nunc International K.K., Tokyo, Japan, where an anti-Fc antibody had been adhered to the wall surface. To the tube was added an adequate amount of the phage obtained in Experiment 1-1, and the mixture was allowed to stand at 4° C. for two hours, followed by washing the tube with phosphate buffered saline containing 0.05% (v/v) of Tween 20 and further with phosphate buffered saline. Thereafter, the phage protein adhered to the IFNAR2 was eluted with 0.1 M aqueous hydrochloric acid solution, and the resulting eluate was collected in another container and neutralized with 1 M Tris (pH 8.0) in a half volume of the aqueous hydrochloric acid solution used. The collected phage was infected with *E. coli*, TG-1, and the infected *E. coli* was cultured in 2YT medium containing 2% (w/v) of glucose and 100 μg/ml of ampicillin, and admixed with helper phage, M13K07, similarly as in Experiment 1-1 to release phage. *E. coli*, TG-1, was infected with a phage clone obtained by repeating the above panning procedure twice, and the infected *E. coli* was inoculated to a plate with 2YT medium containing 2% (w/v) of glucose and 100 μg/ml of ampicillin, cultured at 37° C. for 10 hours, and isolated by collecting colonies. According to conventional manner, plasmids derived from intracellular phages were collected and decoded for their nucleotide sequences by conventional DNA sequencing method. As a result, 12 mutants in Table 2 were selected.

TABLE 2

| | Number of amino acid | | | | | | |
|---|---|---|---|---|---|---|---|
| | 30 | 33 | 145 | 146 | 149 | 150 | Note |
| IFN-α8 | L | R | R | A | M | R | Wild type |
| Mutant No.1 | — | — | L | N | Y | — | MUT1 |
| Mutant No.2 | — | — | I | S | Y | — | MUT2 |
| Mutant No.3 | — | — | L | S | Y | — | MUT3 |
| Mutant No.4 | — | — | V | N | Y | — | MUT4 |
| Mutant No.5 | — | — | V | S | Y | K | |
| Mutant No.6 | — | — | L | S | H | — | |
| Mutant No.7 | — | — | — | — | S | — | |
| Mutant No.8 | — | — | V | N | Y | K | |
| Mutant No.9 | — | — | I | N | Y | — | |
| Mutant No.10 | V | — | I | N | Y | — | |
| Mutant No.11 | — | — | — | — | Q | — | |
| Mutant No.12 | A | — | I | N | Y | — | |

Experiment 1-3

Preparation of Mutant Proteins

In accordance with the method in Experiment 1-1, by using as primers the oligonucleotides represented by SEQ ID NOs: 16 and 17, DNAs among the DNAs encoding the 12 mutant proteins in Table 2, which were specific to the primers' sequences, were amplified and digested with restriction enzymes NdeI and BamHI. The resultant was introduced into the above restriction enzyme sites present in "pET-3a", a product name of a plasmid vector having T7 promotor region, T7 terminator region, ampicillin resistant region, and ColE1 • Ori region, commercialized by EMD Bioscience, USA. The plasmid vector was introduced into a strain of *E. coli*, BL21DE3, to obtain an *E. coli* for the production of wild-type IFN-α8 or any one of the mutant proteins. The microorganism thus obtained was cultured in T-broth in usual manner and centrifuged for collecting proliferated cells. The collected cells were washed twice with TES buffer (pH 8.0) containing 20 mM Tris-HCl, 10 mM of ethylenediamine tetraacetic acid, and 0.5 M of sodium chloride, added to TES buffer (pH 8.0) containing 0.2 mg/ml of lysozyme, treated with ultrasonic in usual manner, and centrifuged to collect a precipitate containing IFN-α8. The precipitate was added to TES buffer containing 1% (w/v) of Triton X-100 and treated thrice with successive stirring and centrifuging to remove supernatant. The obtained sediment was added to 50 mM Tris-HCl buffer (pH 7.0) containing 8 M guanidine hydrochloric acid and 50 mM dithiothreitol, stirred at ambient temperature for 16 hours under light-shielded conditions, and centrifuged to collect a supernatant. The supernatant was gradually added while stirring by small portions to 100-fold volumes of 1 M Tris, 0.9% (w/v) sodium chloride, 0.4 M L-arginine hydrochloric acid, 2.5 mM reduced glutathione, 0.5 mM oxidized glutathione, 0.05% (w/v) Tween 20, and allowed to stand at 4° C. for 16 hours. The resulting mixture was added to four-fold volumes of phosphate buffered saline (pH 7.2) containing 0.1% (w/v) calf serum albumin, adjusted to a pH of 6.5 to 7.5, and subjected to "POROS DEAE", a product name of an anion exchange column chromatography commercialized by Perceptive Biosystems Inc., USA, to collect fractions with IFN-α activity. The fractions were further purified on "SUPERDEX 75", a product name of gel filtration chromatography commercialized by Amersham Biosciences K.K., Tokyo, Japan, to collect fractions with IEN-U activity. Thus, the wild-type IFN-α8 and mutant proteins were obtained.

Experiment 1-4

Anti-Viral Activity

The wild-type IFN-α8 and the 12 mutant proteins, obtained in Experiment 1-3, were assayed for their anti-viral activity. The specific activities thereof were assayed by the following two assays; a conventional assay using a human IFN-α international standard specimen as a standard specimen, FL cells, and sindbis virus; and a bioassay using LS174T cells derived from human rectum carcinoma (Institute of Development, Aging and Cancer Tohoku University, KG0406) and VSV. As a control, "INTRON A", a product name of a recombinant IFN-α2 preparation commercialized by Schering-Plough K.K., Osaka, Japan, and "ADVAFERON", a consensus IFN-α preparation commercialized by Astellas Pharma Inc., Tokyo, Japan. For each assayed values, relative values thereof were calculated based on the activity of the wild-type IFN-α8 being regarded as 100. The results are in Table 3.

TABLE 3

| | Specific activity based on anti-viral activity (IU/mg) | |
|---|---|---|
| | FL | LS174T |
| IFN-α8 (Wild-type) | $2.5 \times 10^8$ (100%) | $5.5 \times 10^8$ (100%) |
| Recombinant IFN-α2 preparation | $1.9 \times 10^8$ (76%) | $8.8 \times 10^7$ (16%) |
| Consensus IFN-α preparation | $4.7 \times 10^8$ (188%) | $4.0 \times 10^8$ (73%) |
| Mutant No. 1 | $2.9 \times 10^8$ (116%) | $3.1 \times 10^9$ (564%) |
| Mutant No. 2 | $4.2 \times 10^8$ (168%) | $4.8 \times 10^9$ (873%) |
| Mutant No. 3 | $3.9 \times 10^8$ (156%) | $6.6 \times 10^9$ (1200%) |
| Mutant No. 4 | $3.3 \times 10^8$ (132%) | $4.1 \times 10^9$ (745%) |
| Mutant No. 5 | $4.4 \times 10^8$ (176%) | $1.6 \times 10^9$ (291%) |
| Mutant No. 6 | $3.0 \times 10^8$ (120%) | $9.5 \times 10^8$ (173%) |
| Mutant No. 7 | $5.0 \times 10^8$ (200%) | $9.0 \times 10^8$ (164%) |
| Mutant No. 8 | $1.8 \times 10^8$ (72%) | $7.5 \times 10^8$ (136%) |
| Mutant No. 9 | $1.0 \times 10^8$ (40%) | $4.4 \times 10^8$ (80%) |
| Mutant No. 10 | $2.9 \times 10^8$ (116%) | $3.5 \times 10^8$ (64%) |
| Mutant No. 11 | $1.7 \times 10^8$ (68%) | $1.5 \times 10^8$ (27%) |
| Mutant No. 12 | $2.4 \times 10^8$ (96%) | $1.1 \times 10^8$ (20%) |

As shown in Table 3, the mutant proteins Nos. 1 to 7 had a higher anti-viral activity than that of the wild-type IFN-α8 in the FL/sindbis assay system and the LS174T/VSV assay system, particularly, they had a remarkably higher activity in the LS174T/VSV assay system by about 2 to 12 times of that of the wild-type IFN α8.

Experiment 1-5
Cell Proliferation Inhibitory Activity

Among the above mutant proteins, the mutant protein No. 1, 2, 3 or 4 was determined for its cell proliferation inhibitory activity on any of Daudi cell (ATCC CCL-213) derived from a human B-cell, U937 cell (JCRB JCRB9021) derived from human chronic myeloid leukemia, Jurkat cell (ATCC TIB-152) derived from human T-cell, PLC/PRF/5 cell (JCRB JCRB0406) derived from human liver carcinoma, LS174T cell (IDAC TKG0406) derived from human colon cancer, EBC-1 cell (JCRB JCRB0820) derived from human lung cancer, MKN1 cell (JCRB JCRB0252) derived from human gastric cancer, ACHN cell (ATCC CRL1611) derived from human renal cancer, VMRC-RCW cell (JCRB JCRB0813), A498 cell (DSMZ ACC55), Caki-1 cell (ATCC HTB46), and HT1197 cell (ATCC CRL-1473) derived from human bladder cancer, which were obtained from American Type Culture Collection (ATCC), Japanese Collection of Research Bioresources (JCRB), German Collection of Microorganisms and Cell Cultures (DSMZ), and Institute of Development, Aging and Cancer Tohoku University (IDAC). The above cell lines were respectively inoculated into RPMI1640 medium containing 10% (v/v) fetal calf serum to give a cell concentration of $8\times10^3$ to $2\times10^5$ cells/ml, admixed with any one of the above four mutant proteins in an amount ranging from 40 pg to 10 μg/ml by stepwisely diluting with the index of anti-viral activity of Experiment 1-4, and incubated at 37° C. for 72 to 120 hours under 5% $CO_2$ gas conditions. The resulting cultures were subjected to "CELL-COUNTING KIT-8", commercialized by Wako Pure Chemical Industries, Ltd., Osaka, Japan, for counting living cells, followed by calculating a concentration required for inhibiting the growth by 50% ($IC_{50}$). As a control, the wild-type IFN-α8 obtained in Experiment 1-3 or a commercialized IFN-α2 preparation and a consensus IFN-α preparation was used similarly as in Experiment 1-4. The results are in Table 4.

TABLE 4

| | Cell-proliferation inhibitory activity ($IC_{50}$) ng/ml | | | | | | | | | | | |
|---|---|---|---|---|---|---|---|---|---|---|---|---|
| | Daudi | U937 | Jurkat | PLC/PRF/5 | LS174T | EBC-1 | MKN1 | ACHN | VMRC-RCW | A498 | Caki-1 | HT1197 |
| IFN-α8 (Wild type) | 0.007 | 1.2 | 0.40 | 0.42 | 25 | 3.0 | 0.033 | 2.9 | 0.50 | 1.3 | 3.9 | 0.31 |
| Recombinant IFN-α2 preparation | 0.01 | 4.2 | 3.4 | 2.2 | >333 | >333 | 0.094 | 18 | 2.9 | 1.2 | 6.1 | 2.0 |
| Consensus IFN-α preparation | — | — | 0.49 | — | 34 | 110 | 0.018 | 2.3 | 0.49 | 0.18 | 0.80 | 0.21 |
| Mutant No.1 (MUT1) | 0.018 | 0.58 | 0.060 | 0.11 | 1.8 | 9.5 | 0.004 | 0.14 | 0.060 | 0.018 | 0.12 | 0.030 |
| Mutant No.2 (MUT2) | 0.009 | 0.070 | 0.020 | 0.010 | 0.70 | 2.3 | 0.002 | 0.030 | 0.020 | 0.007 | 0.050 | 0.010 |
| Mutant No.3 (MUT3) | 0.007 | 0.060 | 0.020 | 0.010 | 0.70 | 1.6 | 0.002 | 0.030 | 0.010 | 0.006 | 0.040 | 0.010 |
| Mutant No.4 (MUT4) | 0.014 | 0.47 | 0.070 | 0.13 | 1.5 | 7.8 | 0.003 | 0.15 | 0.050 | 0.016 | 0.11 | 0.020 |

In the table, the symbol "—" means that no measurement was done.

As shown in Table 4, it was revealed that the mutant proteins Nos. 1, 2, 3 and 4 exhibit a stronger cell proliferation inhibitory activity on a variety of cell lines than that of the wild-type IFN-α8. Comparing with the recombinant IFN-α2 preparation and the consensus IFN-α preparation, the mutant proteins Nos. 1, 2, 3 and 4 had a higher cell proliferation inhibitory activity on any of the cell lines. These results clearly show that the mutant proteins Nos. 1, 2, 3 and 4 have a superior biological activity to the wild-type IFN-α8 and the conventional IFN-α preparations.

Experiment 2

Preparation of Lysine-Replaced Mutant Protein of Mutant IFN-α Protein

Experiment 2-1

Preparation of Phage Library

To determine the conjunct site with a water-soluble polymer, a lysine-replaced mutant protein, where the lysine residues in a mutant IEN-a protein were replaced with other amino acid residue(s), was prepared. Using as a template the DNA (SEQ ID NO:11) encoding the mutant protein of the mutant No. 2, "MUT2", obtained in Experiment 2, an oligonucleotide primer having the nucleotide sequence of SEQ ID NO:25 as a primer for converting the lysine residues at the 46$^{th}$, 50$^{th}$ and 71$^{st}$ into random amino acid residues, and another oligonucleotide primer having the nucleotide sequence of SEQ ID NO:26 as a primer for converting the lysine residues at the 122$^{nd}$, 134$^{th}$, and 135$^{th}$ into random amino acid residues were subjected to PCR in combination. The resulting proliferated DNA as a template was subjected to PCR using an oligonucleotide primer having the nucleotide sequence of SEQ ID NO:27 as a primer for converting the lysine residue at the 31$^{th}$ into a random amino acid residue, and another oligonucleotide primer having the nucleotide sequence of SEQ ID NO:28 as a primer for converting the lysine residues at the 160$^{th}$, 163$^{rd}$ and 165$^{th}$ into random amino acid residues in combination. The above procedure gave a DNA having the nucleotide sequence of SEQ ID NO:29 where 10 lysine residues in the mutant IFN-α protein, "MUT2", had been replaced with codons (NNS) for random amino acid residues. The DNA thus obtained was introduced into a phagemid vector, PCANTAB 5E, to obtain a phage library which was then introduced into *E. coli*, TG-1, by conventional electroporation. The resulting *E. coli* was suspended in 2YT medium containing 2% (w/v) of glucose, cultured while stirring at 37° C. for one hour, inoculated to an LB plate containing 2% (w/v) of glucose and 100 μg/ml of ampicillin, and cultured for 16 hours. All the colonies emerged on the plate were collected; suspended in 2YT medium containing 2% (w/v) of glucose and 100 μg/ml of ampicillin; cultured at 37° C. under stirring conditions; admixed with a helper phage, M13K07, when reaching a turbidity of 0.5; and then cultured while stirring at 37° C. for one hour. The resulting culture was centrifuged to collect cells, and after replacing the culture medium with 2YT medium containing 50 μg/ml of kanamycin and 100 μg/ml of ampicillin, the cells were cultured under stirring conditions at 37° C. for seven hours to produce phages and to obtain a phage library. Similarly as in Experiment 1-2, the phages were screened by panning method using a polyethylene immunotube to which a fusion protein (SEQ ID NO:24) of IFNAR2 and Fc region of immunoglobulin G had been bound. As a result, a lysine-replaced mutant, "MUT2K31" (SEQ ID NO:8) where only the lysine residue at the 31$^{st}$ had not been replaced with other amino acid, and a lysine-replaced mutant, "MUT2K134" (SEQ ID NO:9) where only the lysine residue at the 134$^{th}$ had not been replaced with other amino acid, were obtained. The mutants thus obtained were lysine-replaced mutants where either of the lysine residues at the 31$^{st}$ and 134$^{th}$ and all the remaining lysine residues in the amino acid sequence (SEQ ID NO:5) of mutant IFN-α protein, "MUT2", had been replaced with other amino acid residues.

Experiment 2-2

Preparation of Lysine-Replaced Mutant

The two types of lysine-replaced mutant proteins obtained in the above were expressed in *E. coli* according to the method in Experiment 1-3, except for using as templates a DNA (SEQ ID NO:14) encoding "MUT2K31" or a DNA (SEQ ID NO:15) encoding "MUT2K134", and using as primers oligonucleotides consisting of any one of the nucleotide sequences of SEQ ID NOs:16 and 30, or oligonucleotides consisting of any one of the nucleotide sequences of SEQ ID NOs:16 and 31.

Experiment 2-3

Anti-Viral Activity

The lysine-replaced mutant proteins thus obtained were assayed for anti-viral activity similarly as in Experiment 1-4. As a control, using the wild-type IFN-α8 and the mutant IFN-α protein, "MUT2", prepared in Experiment 1-3, the relative activities of the mutant proteins were calculated. The results are in Table 5.

TABLE 5

| | Specific activity based on anti-viral activity (IU/mg) | |
|---|---|---|
| | FL | LS174T |
| IFN-α8 (Wild type) | $2.5 \times 10^8$ (100%) | $5.5 \times 10^8$ (100%) |
| MUT2 | $4.2 \times 10^8$ (168%) | $4.8 \times 10^9$ (873%) |
| MUT2K31 | $3.4 \times 10^8$ (136%) | $1.1 \times 10^9$ (200%) |
| MUT2K134 | $3.2 \times 10^8$ (128%) | $1.1 \times 10^9$ (200%) |

In accordance with Experiment 1-5, the lysine-replaced mutant proteins thus obtained were assayed for cell-proliferation inhibitory activity against U937 cell, Jurkat cell, PLC/PRF/5 cell, EBC-1 cell, MKN1 cell, ACHN cell, VMRC-RCW cell, A498 cell, Caki-1 cell, or HT1197 cell and determined for their respective $IC_{50}$ similarly as in Experiment 1-5. The results are in Table 6.

TABLE 6

| | Cell-proliferation inhibitory activity ($IC_{50}$) ng/ml | | | | | | | | | |
|---|---|---|---|---|---|---|---|---|---|---|
| | U937 | Jurkat | PLC/ PRF/5 | EBC-1 | MKN1 | ACHN | VMRC- RCW | A498 | Caki-1 | HT1197 |
| IFN-α8 (Wild type) | 1.2 | 0.40 | 0.42 | 3.0 | 0.033 | 2.9 | 0.50 | 1.3 | 3.9 | 0.31 |
| MUT2 | 0.070 | 0.020 | 0.010 | 2.3 | 0.002 | 0.030 | 0.020 | 0.007 | 0.050 | 0.010 |
| MUT2K31 | 3.1 | 0.46 | 0.29 | 5.0 | 0.031 | 1.3 | 0.41 | 0.27 | 0.70 | 0.37 |
| MUT2K134 | 1.2 | 0.32 | 0.18 | 3.3 | 0.022 | 0.72 | 0.4 | 0.20 | 0.47 | 0.27 |

As shown in Tables 5 and 6, the lysine-replaced mutant IFN-αproteins, "MUT2K31" and "MUT2K134", had a reduced anti-viral activity and cell-proliferation inhibitory activity compared with those of original mutant protein, "MUT2", while they had a higher anti-viral activity and cell-proliferation inhibitory activity than those of the wild-type IFN-α8.

Experiment 3

Physiologically Active Complex of Lysine-Replaced Mutant Protein and Water-Soluble Polymer

Experiment 3-1

Preparation of Physiologically Active Complex

A polyethylene glycol having a molecular weight of 20 kDa was conjugated to the lysine-replaced mutant protein obtained by the method in Experiment 2-2 or the wild-type IFN-α8 obtained in Experiment 1-3: The wild-type IFN-α8, mutant IFN-α protein, "MUT2K31", or mutant IFN-α protein, "MUT2K134", was dissolved in borate buffer (pH 9.0) to give a concentration of 0.1 to 5 mg/ml, admixed with polyethylene glycol activated with monomethoxy N-succine-imidyl propionate (m-PEG-SPA) as a water-soluble polymer in a molar ratio of 3 to 8 times of each protein, and allowed to react at 7° C. for two hours. To the mixture was added ϵ-aminocaproic acid in an amount of 10 times of the water-soluble polymer by molar ratio, and the resulting mixture was allowed to stand for some time before suspending the reaction. Then, the reaction mixture was fractionated on HPLC using "RESOURCE Q", a column for anion-exchange chromatography Amrersham Biosciences K.K., Tokyo, Japan, to remove polyethylene glycol free of conjugating with protein. The resultant was further fractionated on HPLC using "SUPERDEX 200", a column for gel filtration chromatography commercialized by Amersham Biosciences K.K., Tokyo, Japan, followed by collecting a physiologically active complex composed of one molar of IFN-α8 or IFN-α to which one molar of polyethylene glycol was conjugated.

Experiment 3-2

Thermal Stability

Using MEM medium containing 5% (v/v) of fetal calf serum, the physiologically active complexes were prepared into solutions with a concentration of 10,000 IU/ml and treated by heating at the temperatures as indicated in Table 7 below for 30 min. After centrifugation, the resulting supernatants were collected and subjected to an assay system using FL cells and sindbis virus to determine the residual anti-viral activity. The percentage (the residual activity ratio) of each complex was calculated with the following equation. The results are in Table 7.

Residual activity ratio (%)={(Virus infection inhibitory activity after heat treatment)/(Virus infection inhibitory activity before heat treatment)}×100 Equation 1

TABLE 7

| | Residual activity ratio (%) | | | | | |
|---|---|---|---|---|---|---|
| | MUT2K31 | MUT2K31-PEG (20 kDa) | MUT2K134 | MUT2K134-PEG (20 kDa) | IFN-α8 (Wild type) | IFN-α8-PEG (20 kDa) |
| Before treatment | 100 | 100 | 100 | 100 | 100 | 100 |
| 40° C. | 122 | 96 | 107 | 108 | 97 | 100 |
| 50° C. | 101 | 101 | 106 | 98 | 94 | 100 |
| 60° C. | 18 | 69 | 36 | 84 | 15 | 61 |
| 70° C. | 0.7 | 2.6 | 0.7 | 4.5 | 0.1 | 1.2 |

As shown in Table 7, "MUT2K31" or "MUT2K134" conjugated with polyethylene glycol retained 69% or 84% activity even after the treatment at 60° C., and this revealed that these mutants were superior in stability to the wild-type IFN-α8 conjugated with polyethylene glycol.

Experiment 3-3

Biological Action of Physiologically Active Complex of Lysine-Replaced Mutant Protein and Water-Soluble Polymer In accordance with the methods in Experiments 1-4 and 1-5, the anti-viral activity and the cell proliferation activity of physiologically active complexes were respectively examined. As a control, "PEGASYS", a product name of an IFN-α preparation of IFN-α2a conjugated with polyethylene glycol having a molecular weight of 40 kDa commercialized by Chugai Pharmaceutical Co., Ltd., Tokyo, Japan. The results of the anti-viral activity and the cell proliferation inhibitory activity of the complexes are respectively in Tables 8 and 9.

TABLE 8

| | Specific activity based on anti-viral activity (IU/mg) | |
|---|---|---|
| | FL | LS174T |
| Recombinant IFN-α2a-PEG (40 kDa) | $2.86 \times 10^6$ (100%) | $9.01 \times 10^5$ (100%) |
| MUT2K31-PEG (20 kDa) | $1.72 \times 10^7$ (601%) | $2.00 \times 10^7$ (2220%) |
| MUT2K134-EG (20 kDa) | $2.79 \times 10^7$ (976%) | $4.73 \times 10^7$ (5250%) |

TABLE 9

| | Cell-proliferation inhibitory activity ($IC_{50}$) ng/ml | | | | | | | | | |
|---|---|---|---|---|---|---|---|---|---|---|
| | U937 | Jurkat | PLC/PRF/5 | EBC-1 | MKN1 | ACHN | VMRC-RCW | A498 | Caki-1 | HT1197 |
| Recombinant IFN-α2a-PEG (40 kDa) | 430 | 400 | 190 | 1600 | 32 | 2800 | 290 | 690 | 1900 | 150 |
| MUT2K31-PEG (20 kDa) | 64 | 33 | 6.0 | 100 | 1.3 | 91 | 16 | 33 | 93 | 7.1 |
| MUT2K134-PEG (20 kDa) | 7.3 | 4.4 | 0.93 | 13 | 0.26 | 11 | 3.1 | 6.1 | 19 | 1.0 |

As shown in Tables 8 and 9, the physiologically active complexes prepared by conjugating polyethylene glycol to "MUT2K31" and "MUT2K134" had a distinctly higher anti-viral activity and cell proliferation inhibitory activity than those of IFN-2α preparation.

Experiment 4

Acute Toxicity Test

According to conventional manner, any one of the mutant IFN-(protein, "MUT1", "MUT2", "MUT3" or "MUT4" obtained in Experiment 1-3; the lysine-replaced mutant protein of the mutant IFN-α protein, "MUT2", "MUT2K31", or "MUT2K134" obtained in Experiment 2-2; and the physiologically active complex of "MUT2K31" or "MUT2K134" to which one molar polyethylene glycol was conjugated, was administered percutaneously, perorally, or peritoneally by injection to male mice, 8-week-old, weighing 20 to 25 g. The $LD_{50}$ of each of the complexes was at least 1 mg/kg body weight, independently of the above administration routes. The result indicates that the physiologically active complexes of the present invention can be safely used as pharmaceuticals or incorporated into pharmaceuticals, which are directed to be administered to humans.

The following Examples explain the present invention in detail:

Example 1

Liquid Preparation

Any one of the physiologically active complexes, which had been produced by conjugating any one of the mutant IFN-α protein, "MUT1", "MUT2", "MUT3" or "MUT4", prepared in Experiment 1-3; "MUT2K31" or "MUT2K134", a lysine-replaced mutant protein of the mutant IFN-α protein of "MUT2", prepared in Experiment 2-2; and "MUT2K31" or "MUT2K134", a physiologically active complex conjugated with one molecule of polyethylene glycol, prepared in Experiment 3-1, was dissolved in physiological saline containing 1% (w/v) of human serum albumin as a stabilizer to give a concentration of 1 mg/ml, and sterilized by usual microfiltration to obtain a liquid preparation.

The product is useful as an injection preparation, eye drop preparation, and nose drop preparation for treating or preventing susceptive diseases including malignant tumors, viral diseases, bacterial diseases, and immunological diseases.

Example 2

Dried Injection Preparation

One hundred milligrams of any one of the physiologically active complexes, which had been produced by conjugating any one of the mutant IFN-α protein, "MUT1", "MUT2", "MUT3" or "MUT4", prepared in Experiment 1-3; "MUT2K31" or "MUT2K134", a lysine-replaced mutant protein of the mutant IFN-α protein of "MUT2", prepared in Experiment 2-2; and "MUT2K31" or "MUT2K1334", a physiologically active complex conjugated with one molecular of polyethylene glycol, prepared in Experiment 3-1, was dissolved in 100 ml of physiological saline containing 1% (w/v) of a purified gelatin as a stabilizer, sterilized by usual microfiltration, distributed into vials by one milliliter, lyophilized, and sealed to obtain a dried injection preparation.

The product is useful as a dried injection preparation for treating or preventing susceptive diseases including malignant tumors, viral diseases, bacterial diseases, and immunological diseases.

Example 3

Ointment

"HIVISWAKO", a product name of carboxy vinyl polymer commercialized by Wako Pure Chemicals Co., Osaka, Japan, and "TPEHA®", a pyrogen-free highly purified trehalose commercialized by Hayashibara Shoji, Ltd., Okayama, Japan, were dissolved in sterilized distilled water to give respective concentrations of 1.4% (w/v) and 2.0% (w/v). The resulting solution was mixed to homogeneity with an appropriate amount of any one of the physiologically active complexes which were produced by conjugating any one of the mutant IFN-α protein, "MUT1", "MUT2", "MUT3" or "MUT4", prepared in Experiment 1-3; "MUT2K31" or "MUT2K134", a lysine-replaced mutant protein of "MUT2", prepared in Experiment 2-2; and "MUT2K31" or "MUT2K134", a physiologically-active complex conjugated with one molar polyethylene glycol, prepared in Experiment 3-1. The resulting mixture was adjusted to pH 7.2 to obtain a paste product containing about 5 μg/g of any one of the physiologically active complexes.

The product having a satisfactory extendability and stability is useful as an ointment for treating or preventing susceptive diseases such as malignant tumors, viral diseases, bacterial diseases, and immunological diseases.

Example 4

Tablet

An appropriate amount of any one of the physiologically active complexes which were produced by conjugating any one of the mutant IFN-α protein, "MUT1", "MUT2", "MUT3" or "MUT4", prepared in Experiment 1-3; "MUT2K31" or "MUT2K134", a lysine-replaced mutant protein of the mutant IFN-α protein of "MUT2", prepared in Experiment 2-2; and "MUT2K31" or "MUT2K134", a physiologically active complex conjugated with one molar polyethylene glycol, prepared in Experiment 3-1, was homogeneously mixed with "FINETOSE", an anhydrous crystalline α-maltose powder commercialized by Hayashibara Shoji Ltd., Okayama, Japan. The resulting mixture was tabletted in usual manner to obtain a tablet, weighing about 200 mg, containing about 1 μg of any one of the physiologically active complexes.

The product having a satisfactory intake property and stability is useful as a tablet for treating or preventing susceptive diseases such as malignant tumors, viral diseases, bacterial diseases, and immunological diseases.

INDUSTRIAL APPLICABILITY

As explained above, the mutant IFN-α proteins of the present invention have a quite higher activity compared with conventional IFN-α preparations, and, when conjugated with water-soluble polymers into physiologically active complexes, they exhibit a superior dynamics in living bodies and have a sustained high-blood-concentration-level for a relatively long period of time even when administered by injection. Thus, the present invention provides agents for susceptive diseases superior in anti-viral and anti-tumor actions compared with conventional agents for susceptive diseases, containing IFN-α as an effective ingredient, and have a variety of uses such as agents against tumors, viral diseases, and infection diseases, as well as agents for immunological diseases.

The invention claimed is:

1. A mutant protein comprising an amino acid sequence of human interferon-α subtype α8 of any one of SEQ ID NOs:1 to 3, where the arginine residue at the $145^{th}$ has been replaced with leucine, isoleucine, or valine residue; the alanine residue at the $146^{th}$ has been replaced with asparagine or serine residue; and the methionine residue at the $149^{th}$ has been replaced with tyrosine residue.

2. The mutant protein of claim 1, comprising any one of the amino acid sequences of SEQ ID NOs:4 to 7.

3. The mutant protein of claim 1, comprising an amino acid sequence represented by any one of SEQ ID NOs:1 to 3, where either of the lysine residues at the $31^{st}$ and $134^{th}$ has been retained but the remaining lysine residues have been replaced with other amino acid residue(s).

4. The mutant protein of claim 3, comprising an amino acid sequence represented by SEQ ID NO: 8 or 9.

5. A physiologically active complex, in which a mutant protein of claim 1 has been conjugated with a water-soluble polymer.

6. A pharmaceutical composition, comprising a mutant protein of claim 1 and a suitable excipient.

* * * * *

SEQUENCE LISTING

```
<160> NUMBER OF SEQ ID NOS: 31

<210> SEQ ID NO 1
<211> LENGTH: 166
<212> TYPE: PRT
<213> ORGANISM: human
<220> FEATURE:
<221> NAME/KEY: misc_feature
<223> OTHER INFORMATION: IFN-alpha 8a

<400> SEQUENCE: 1

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
```

-continued

```
                85                  90                  95

Glu Val Leu Cys Asp Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165


<210> SEQ ID NO 2
<211> LENGTH: 166
<212> TYPE: PRT
<213> ORGANISM: human
<220> FEATURE:
<221> NAME/KEY: misc_feature
<223> OTHER INFORMATION: IFN-alpha 8b

<400> SEQUENCE: 2

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Arg Leu Lys Ser Lys Glu
                165


<210> SEQ ID NO 3
<211> LENGTH: 161
<212> TYPE: PRT
<213> ORGANISM: human
<220> FEATURE:
<221> NAME/KEY: misc_feature
<223> OTHER INFORMATION: IFN-alpha 8c

<400> SEQUENCE: 3

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
```

-continued

```
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Arg Ala Glu Ile Met Arg Ser Phe Ser Leu Ser Ile Asn Leu Gln Lys
145                 150                 155                 160

Asp


<210> SEQ ID NO 4
<211> LENGTH: 166
<212> TYPE: PRT
<213> ORGANISM: Artificial Sequence
<220> FEATURE:
<223> OTHER INFORMATION: Synthetic

<400> SEQUENCE: 4

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Leu Asn Glu Ile Tyr Arg Ser Phe Ser Leu Ser Ile Asn Leu Gln Lys
145                 150                 155                 160

Arg Leu Lys Ser Lys Glu
                165


<210> SEQ ID NO 5
<211> LENGTH: 166
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT2)
```

-continued

<400> SEQUENCE: 5

```
Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Ile Ser Glu Ile Tyr Arg Ser Phe Ser Leu Ser Ile Asn Leu Gln Lys
145                 150                 155                 160

Arg Leu Lys Ser Lys Glu
                165
```

<210> SEQ ID NO 6
<211> LENGTH: 166
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT3)

<400> SEQUENCE: 6

```
Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Leu Ser Glu Ile Tyr Arg Ser Phe Ser Leu Ser Ile Asn Leu Gln Lys
145                 150                 155                 160

Arg Leu Lys Ser Lys Glu
```

-continued

```
                165

<210> SEQ ID NO 7
<211> LENGTH: 166
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT4)

<400> SEQUENCE: 7

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Lys Gln Phe
        35                  40                  45

Gln Lys Ala Gln Ala Ile Ser Val Leu His Glu Met Ile Gln Gln Thr
    50                  55                  60

Phe Asn Leu Phe Ser Thr Lys Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95

Glu Ser Cys Val Met Gln Glu Val Gly Val Ile Glu Ser Pro Leu Met
            100                 105                 110

Tyr Glu Asp Ser Ile Leu Ala Val Arg Lys Tyr Phe Gln Arg Ile Thr
        115                 120                 125

Leu Tyr Leu Thr Glu Lys Lys Tyr Ser Ser Cys Ala Trp Glu Val Val
    130                 135                 140

Val Asn Glu Ile Tyr Arg Ser Phe Ser Leu Ser Ile Asn Leu Gln Lys
145                 150                 155                 160

Arg Leu Lys Ser Lys Glu
                165


<210> SEQ ID NO 8
<211> LENGTH: 166
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT2K31)

<400> SEQUENCE: 8

Cys Asp Leu Pro Gln Thr His Ser Leu Gly Asn Arg Arg Ala Leu Ile
1               5                   10                  15

Leu Leu Ala Gln Met Arg Arg Ile Ser Pro Phe Ser Cys Leu Lys Asp
            20                  25                  30

Arg His Asp Phe Glu Phe Pro Gln Glu Glu Phe Asp Asp Gly Gln Phe
        35                  40                  45

Gln Arg Ala Gln Ala Ile Ser Val Leu His Glu Met Ile Gln Gln Thr
    50                  55                  60

Phe Asn Leu Phe Ser Thr Gly Asp Ser Ser Ala Ala Leu Asp Glu Thr
65                  70                  75                  80

Leu Leu Asp Glu Phe Tyr Ile Glu Leu Asp Gln Gln Leu Asn Asp Leu
                85                  90                  95
```

-continued

Glu Ser Cys Val Met Gln Glu Val Gly Val Ile Glu Ser Pro Leu Met
100 105 110

Tyr Glu Asp Ser Ile Leu Ala Val Arg Arg Tyr Phe Gln Arg Ile Thr
115 120 125

Leu Tyr Leu Thr Glu His Thr Tyr Ser Ser Cys Ala Trp Glu Val Val
130 135 140

Ile Ser Glu Ile Tyr Arg Ser Phe Ser Leu Ser Ile Asn Leu Gln Gly
145 150 155 160

Arg Leu Leu Ser Pro Glu
165

<210> SEQ ID NO 9
<211> LENGTH: 166
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT2K134)

<400> SEQUENCE: 9

Cys Asp Leu Pro Gln Thr His Ser Leu Gly Asn Arg Arg Ala Leu Ile
1 5 10 15

Leu Leu Ala Gln Met Arg Arg Ile Ser Pro Phe Ser Cys Leu Ala Asp
20 25 30

Arg His Asp Phe Glu Phe Pro Gln Glu Glu Phe Asp Asp His Gln Phe
35 40 45

Gln Asn Ala Gln Ala Ile Ser Val Leu His Glu Met Ile Gln Gln Thr
50 55 60

Phe Asn Leu Phe Ser Thr Val Asp Ser Ser Ala Ala Leu Asp Glu Thr
65 70 75 80

Leu Leu Asp Glu Phe Tyr Ile Glu Leu Asp Gln Gln Leu Asn Asp Leu
85 90 95

Glu Ser Cys Val Met Gln Glu Val Gly Val Ile Glu Ser Pro Leu Met
100 105 110

Tyr Glu Asp Ser Ile Leu Ala Val Arg Arg Tyr Phe Gln Arg Ile Thr
115 120 125

Leu Tyr Leu Thr Glu Lys Asp Tyr Ser Ser Cys Ala Trp Glu Val Val
130 135 140

Ile Ser Glu Ile Tyr Arg Ser Phe Ser Leu Ser Ile Asn Leu Gln Arg
145 150 155 160

Arg Leu Ala Ser Thr Glu
165

<210> SEQ ID NO 10
<211> LENGTH: 498
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT1)
<220> FEATURE:
<221> NAME/KEY: mat_peptide
<222> LOCATION: (1)..(498)
<220> FEATURE:
<221> NAME/KEY: CDS
<222> LOCATION: (1)..(498)

<400> SEQUENCE: 10

-continued

```
tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg aag gac       96
Leu Leu Ala Gln Met Arg Arg Ile Ser Pro Phe Ser Cys Leu Lys Asp
            20                  25                  30

aga cat gac ttt gaa ttc ccc cag gag gag ttt gat gat aaa cag ttc      144
Arg His Asp Phe Glu Phe Pro Gln Glu Glu Phe Asp Asp Lys Gln Phe
        35                  40                  45

cag aag gct caa gcc atc tct gtc ctc cat gag atg atc cag cag acc      192
Gln Lys Ala Gln Ala Ile Ser Val Leu His Glu Met Ile Gln Gln Thr
    50                  55                  60

ttc aac ctc ttc agc aca aag gac tca tct gct gct ttg gat gag acc      240
Phe Asn Leu Phe Ser Thr Lys Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg aaa tac ttc caa aga atc act      384
Tyr Glu Asp Ser Ile Leu Ala Val Arg Lys Tyr Phe Gln Arg Ile Thr
        115                 120                 125

cta tat ctg aca gag aag aaa tac agc tct tgt gcc tgg gag gtt gtc      432
Leu Tyr Leu Thr Glu Lys Lys Tyr Ser Ser Cys Ala Trp Glu Val Val
    130                 135                 140

ctg aac gaa atc tac aga tcc ttc tct tta tca atc aac ttg caa aaa      480
Leu Asn Glu Ile Tyr Arg Ser Phe Ser Leu Ser Ile Asn Leu Gln Lys
145                 150                 155                 160

aga ttg aag agt aag gaa                                              498
Arg Leu Lys Ser Lys Glu
                165
```

```
<210> SEQ ID NO 11
<211> LENGTH: 498
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT2)
<220> FEATURE:
<221> NAME/KEY: mat_peptide
<222> LOCATION: (1)..(498)
<220> FEATURE:
<221> NAME/KEY: CDS
<222> LOCATION: (1)..(498)

<400> SEQUENCE: 11
```

```
tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg aag gac       96
Leu Leu Ala Gln Met Arg Arg Ile Ser Pro Phe Ser Cys Leu Lys Asp
            20                  25                  30

aga cat gac ttt gaa ttc ccc cag gag gag ttt gat gat aaa cag ttc      144
Arg His Asp Phe Glu Phe Pro Gln Glu Glu Phe Asp Asp Lys Gln Phe
        35                  40                  45

cag aag gct caa gcc atc tct gtc ctc cat gag atg atc cag cag acc      192
Gln Lys Ala Gln Ala Ile Ser Val Leu His Glu Met Ile Gln Gln Thr
    50                  55                  60
```

-continued

```
ttc aac ctc ttc agc aca aag gac tca tct gct gct ttg gat gag acc      240
Phe Asn Leu Phe Ser Thr Lys Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg aaa tac ttc caa aga atc act      384
Tyr Glu Asp Ser Ile Leu Ala Val Arg Lys Tyr Phe Gln Arg Ile Thr
        115                 120                 125

cta tat ctg aca gag aag aaa tac agc tct tgt gcc tgg gag gtt gtc      432
Leu Tyr Leu Thr Glu Lys Lys Tyr Ser Ser Cys Ala Trp Glu Val Val
    130                 135                 140

atc tcg gaa atc tac aga tcc ttc tct tta tca atc aac ttg caa aaa      480
Ile Ser Glu Ile Tyr Arg Ser Phe Ser Leu Ser Ile Asn Leu Gln Lys
145                 150                 155                 160

aga ttg aag agt aag gaa                                              498
Arg Leu Lys Ser Lys Glu
                165


<210> SEQ ID NO 12
<211> LENGTH: 498
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT3)
<220> FEATURE:
<221> NAME/KEY: mat_peptide
<222> LOCATION: (1)..(498)
<220> FEATURE:
<221> NAME/KEY: CDS
<222> LOCATION: (1)..(498)

<400> SEQUENCE: 12

tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg aag gac       96
Leu Leu Ala Gln Met Arg Arg Ile Ser Pro Phe Ser Cys Leu Lys Asp
            20                  25                  30

aga cat gac ttt gaa ttc ccc cag gag gag ttt gat gat aaa cag ttc      144
Arg His Asp Phe Glu Phe Pro Gln Glu Glu Phe Asp Asp Lys Gln Phe
        35                  40                  45

cag aag gct caa gcc atc tct gtc ctc cat gag atg atc cag cag acc      192
Gln Lys Ala Gln Ala Ile Ser Val Leu His Glu Met Ile Gln Gln Thr
    50                  55                  60

ttc aac ctc ttc agc aca aag gac tca tct gct gct ttg gat gag acc      240
Phe Asn Leu Phe Ser Thr Lys Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg aaa tac ttc caa aga atc act      384
Tyr Glu Asp Ser Ile Leu Ala Val Arg Lys Tyr Phe Gln Arg Ile Thr
        115                 120                 125
```

-continued

```
cta tat ctg aca gag aag aaa tac agc tct tgt gcc tgg gag gtt gtc      432
Leu Tyr Leu Thr Glu Lys Lys Tyr Ser Ser Cys Ala Trp Glu Val Val
    130                 135                 140

ctg agc gaa atc tac aga tcc ttc tct tta tca atc aac ttg caa aaa      480
Leu Ser Glu Ile Tyr Arg Ser Phe Ser Leu Ser Ile Asn Leu Gln Lys
145                 150                 155                 160

aga ttg aag agt aag gaa                                              498
Arg Leu Lys Ser Lys Glu
                165


<210> SEQ ID NO 13
<211> LENGTH: 498
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT4)
<220> FEATURE:
<221> NAME/KEY: mat_peptide
<222> LOCATION: (1)..(498)
<220> FEATURE:
<221> NAME/KEY: CDS
<222> LOCATION: (1)..(498)

<400> SEQUENCE: 13

tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg aag gac       96
Leu Leu Ala Gln Met Arg Arg Ile Ser Pro Phe Ser Cys Leu Lys Asp
            20                  25                  30

aga cat gac ttt gaa ttc ccc cag gag gag ttt gat gat aaa cag ttc      144
Arg His Asp Phe Glu Phe Pro Gln Glu Glu Phe Asp Asp Lys Gln Phe
        35                  40                  45

cag aag gct caa gcc atc tct gtc ctc cat gag atg atc cag cag acc      192
Gln Lys Ala Gln Ala Ile Ser Val Leu His Glu Met Ile Gln Gln Thr
    50                  55                  60

ttc aac ctc ttc agc aca aag gac tca tct gct gct ttg gat gag acc      240
Phe Asn Leu Phe Ser Thr Lys Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg aaa tac ttc caa aga atc act      384
Tyr Glu Asp Ser Ile Leu Ala Val Arg Lys Tyr Phe Gln Arg Ile Thr
        115                 120                 125

cta tat ctg aca gag aag aaa tac agc tct tgt gcc tgg gag gtt gtc      432
Leu Tyr Leu Thr Glu Lys Lys Tyr Ser Ser Cys Ala Trp Glu Val Val
    130                 135                 140

gtc aac gaa atc tac aga tcc ttc tct tta tca atc aac ttg caa aaa      480
Val Asn Glu Ile Tyr Arg Ser Phe Ser Leu Ser Ile Asn Leu Gln Lys
145                 150                 155                 160

aga ttg aag agt aag gaa                                              498
Arg Leu Lys Ser Lys Glu
                165


<210> SEQ ID NO 14
<211> LENGTH: 498
```

-continued

<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT2K31)
<220> FEATURE:
<221> NAME/KEY: mat_peptide
<222> LOCATION: (1)..(498)
<220> FEATURE:
<221> NAME/KEY: CDS
<222> LOCATION: (1)..(498)

<400> SEQUENCE: 14

```
tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg aag gac       96
Leu Leu Ala Gln Met Arg Arg Ile Ser Pro Phe Ser Cys Leu Lys Asp
            20                  25                  30

aga cat gac ttt gaa ttc ccc cag gag gag ttt gat gat ggc cag ttc      144
Arg His Asp Phe Glu Phe Pro Gln Glu Glu Phe Asp Asp Gly Gln Phe
        35                  40                  45

cag cgg gct caa gcc atc tct gtc ctc cat gag atg atc cag cag acc      192
Gln Arg Ala Gln Ala Ile Ser Val Leu His Glu Met Ile Gln Gln Thr
    50                  55                  60

ttc aac ctc ttc agc aca ggg gac tca tct gct gct ttg gat gag acc      240
Phe Asn Leu Phe Ser Thr Gly Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg agg tac ttc caa aga atc act      384
Tyr Glu Asp Ser Ile Leu Ala Val Arg Arg Tyr Phe Gln Arg Ile Thr
        115                 120                 125

cta tat ctg aca gag cac acc tac agc tct tgt gcc tgg gag gtt gtc      432
Leu Tyr Leu Thr Glu His Thr Tyr Ser Ser Cys Ala Trp Glu Val Val
    130                 135                 140

atc tcg gaa atc tac aga tcc ttc tct tta tca atc aac ttg caa ggg      480
Ile Ser Glu Ile Tyr Arg Ser Phe Ser Leu Ser Ile Asn Leu Gln Gly
145                 150                 155                 160

aga ttg ctc agt ccc gaa                                              498
Arg Leu Leu Ser Pro Glu
                165
```

<210> SEQ ID NO 15
<211> LENGTH: 498
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha Mutant Protein (MUT2K134)
<220> FEATURE:
<221> NAME/KEY: mat_peptide
<222> LOCATION: (1)..(498)
<220> FEATURE:
<221> NAME/KEY: CDS
<222> LOCATION: (1)..(498)

<400> SEQUENCE: 15

-continued

```
tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg gcg gac       96
Leu Leu Ala Gln Met Arg Arg Ile Ser Pro Phe Ser Cys Leu Ala Asp
            20                  25                  30

aga cat gac ttt gaa ttc ccc cag gag gag ttt gat gat cac cag ttc      144
Arg His Asp Phe Glu Phe Pro Gln Glu Glu Phe Asp Asp His Gln Phe
        35                  40                  45

cag aac gct caa gcc atc tct gtc ctc cat gag atg atc cag cag acc      192
Gln Asn Ala Gln Ala Ile Ser Val Leu His Glu Met Ile Gln Gln Thr
    50                  55                  60

ttc aac ctc ttc agc aca gtc gac tca tct gct gct ttg gat gag acc      240
Phe Asn Leu Phe Ser Thr Val Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg cgc tac ttc caa aga atc act      384
Tyr Glu Asp Ser Ile Leu Ala Val Arg Arg Tyr Phe Gln Arg Ile Thr
        115                 120                 125

cta tat ctg aca gag aag gac tac agc tct tgt gcc tgg gag gtt gtc      432
Leu Tyr Leu Thr Glu Lys Asp Tyr Ser Ser Cys Ala Trp Glu Val Val
    130                 135                 140

atc tcg gaa atc tac aga tcc ttc tct tta tca atc aac ttg caa cgc      480
Ile Ser Glu Ile Tyr Arg Ser Phe Ser Leu Ser Ile Asn Leu Gln Arg
145                 150                 155                 160

aga ttg gcc agt acg gaa                                              498
Arg Leu Ala Ser Thr Glu
                165
```

<210> SEQ ID NO 16
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (human IFN-alpha 8b)

<400> SEQUENCE: 16
ttccatatgt gtgatctgcc tcagact 27

<210> SEQ ID NO 17
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (human IFN-alpha 8b)

<400> SEQUENCE: 17
tctcctaggt cattccttac tcttcaa 27

<210> SEQ ID NO 18
<211> LENGTH: 498
<212> TYPE: DNA
<213> ORGANISM: Homo sapiens -continued
<220> FEATURE:
<221> NAME/KEY: misc_feature
<223> OTHER INFORMATION: IFN-alpha 8b
<220> FEATURE:
<221> NAME/KEY: mat_peptide
<222> LOCATION: (1)..(498)
<220> FEATURE:
<221> NAME/KEY: CDS
<222> LOCATION: (1)..(498)

<400> SEQUENCE: 18

```
tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg aag gac       96
Leu Leu Ala Gln Met Arg Arg Ile Ser Pro Phe Ser Cys Leu Lys Asp
            20                  25                  30

aga cat gac ttt gaa ttc ccc cag gag gag ttt gat gat aaa cag ttc      144
Arg His Asp Phe Glu Phe Pro Gln Glu Glu Phe Asp Asp Lys Gln Phe
        35                  40                  45

cag aag gct caa gcc atc tct gtc ctc cat gag atg atc cag cag acc      192
Gln Lys Ala Gln Ala Ile Ser Val Leu His Glu Met Ile Gln Gln Thr
    50                  55                  60

ttc aac ctc ttc agc aca aag gac tca tct gct gct ttg gat gag acc      240
Phe Asn Leu Phe Ser Thr Lys Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg aaa tac ttc caa aga atc act      384
Tyr Glu Asp Ser Ile Leu Ala Val Arg Lys Tyr Phe Gln Arg Ile Thr
        115                 120                 125

cta tat ctg aca gag aag aaa tac agc tct tgt gcc tgg gag gtt gtc      432
Leu Tyr Leu Thr Glu Lys Lys Tyr Ser Ser Cys Ala Trp Glu Val Val
    130                 135                 140

aga gca gaa atc atg aga tcc ttc tct tta tca atc aac ttg caa aaa      480
Arg Ala Glu Ile Met Arg Ser Phe Ser Leu Ser Ile Asn Leu Gln Lys
145                 150                 155                 160

aga ttg aag agt aag gaa                                              498
Arg Leu Lys Ser Lys Glu
                165
```

<210> SEQ ID NO 19
<211> LENGTH: 88
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (human IFN-alpha 8b)
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (52)..(53)
<223> OTHER INFORMATION: n is a, c, g, or t

<400> SEQUENCE: 19

```
atactcctgg cacaaatgcg aagaatctct cctttctcct gcnnsaagga cnnscatgac     60
```

-continued tttgaattcc cccaggagga gtttgatg 88

<210> SEQ ID NO 20
<211> LENGTH: 90
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (human IFN-alpha 8b)
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (58)..(59)
<223> OTHER INFORMATION: n is a, c, g, or t

<400> SEQUENCE: 20
ctcttcaatc ttttttgcaa gttgattgat aaagagaagg asnnsnngat ttcsnnsnng 60
acaacctccc aggcacaaga gctgtatttc 90

<210> SEQ ID NO 21
<211> LENGTH: 91
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (human IFN-alpha 8b)

<400> SEQUENCE: 21
aacactccat ggcctgtgat ctgcctcaga ctcacagcct gggtaacagg agggccttga 60
tactcctggc acaaatgcga agaatctctc c 91

<210> SEQ ID NO 22
<211> LENGTH: 75
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (human IFN-alpha 8b)

<400> SEQUENCE: 22
aacactgcgg ccgcggatcc accaccacct tccttactct tcaatctttt ttgcaagttg 60
attgataaag agaag 75

<210> SEQ ID NO 23
<211> LENGTH: 498
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: IFN-alpha 8 Mutant (Library)

-continued

```
<220> FEATURE:
<221> NAME/KEY: mat_peptide
<222> LOCATION: (1)..(498)
<220> FEATURE:
<221> NAME/KEY: CDS
<222> LOCATION: (1)..(498)
<220> FEATURE:
<221> NAME/KEY: misc_feature
<222> LOCATION: (88)..(89)
<223> OTHER INFORMATION: n is a, c, g, or t
<220> FEATURE:
<221> NAME/KEY: misc_feature
<222> LOCATION: (97)..(98)
<223> OTHER INFORMATION: n is a, c, g, or t
<220> FEATURE:
<221> NAME/KEY: misc_feature
<222> LOCATION: (433)..(434)
<223> OTHER INFORMATION: n is a, c, g, or t
<220> FEATURE:
<221> NAME/KEY: misc_feature
<222> LOCATION: (436)..(437)
<223> OTHER INFORMATION: n is a, c, g, or t
<220> FEATURE:
<221> NAME/KEY: misc_feature
<222> LOCATION: (445)..(446)
<223> OTHER INFORMATION: n is a, c, g, or t
<220> FEATURE:
<221> NAME/KEY: misc_feature
<222> LOCATION: (448)..(449)
<223> OTHER INFORMATION: n is a, c, g, or t
<220> FEATURE:
<221> NAME/KEY: misc_feature
<222> LOCATION: (30)..(30)
<223> OTHER INFORMATION: The 'Xaa' at location 30 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (33)..(33)
<223> OTHER INFORMATION: The 'Xaa' at location 33 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (145)..(145)
<223> OTHER INFORMATION: The 'Xaa' at location 145 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (146)..(146)
<223> OTHER INFORMATION: The 'Xaa' at location 146 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (149)..(149)
<223> OTHER INFORMATION: The 'Xaa' at location 149 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (150)..(150)
<223> OTHER INFORMATION: The 'Xaa' at location 150 stands for Lys, Asn,
      Arg, Ser, Thr, Met, Ile, Glu, Asp, Gly, Ala, Val, Gln, His, Pro,
      Leu, Tyr, Trp, Cys, or Phe.

<400> SEQUENCE: 23

tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc nns aag gac       96
Leu Leu Ala Gln Met Arg Arg Ile Ser Pro Phe Ser Cys Xaa Lys Asp
            20                  25                  30

nns cat gac ttt gaa ttc ccc cag gag gag ttt gat gat aaa cag ttc      144
Xaa His Asp Phe Glu Phe Pro Gln Glu Glu Phe Asp Asp Lys Gln Phe
```

-continued

```
        35                  40                  45

cag aag gct caa gcc atc tct gtc ctc cat gag atg atc cag cag acc      192
Gln Lys Ala Gln Ala Ile Ser Val Leu His Glu Met Ile Gln Gln Thr
    50                  55                  60

ttc aac ctc ttc agc aca aag gac tca tct gct gct ttg gat gag acc      240
Phe Asn Leu Phe Ser Thr Lys Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110

tac gag gac tcc atc ctg gct gtg agg aaa tac ttc caa aga atc act      384
Tyr Glu Asp Ser Ile Leu Ala Val Arg Lys Tyr Phe Gln Arg Ile Thr
        115                 120                 125

cta tat ctg aca gag aag aaa tac agc tct tgt gcc tgg gag gtt gtc      432
Leu Tyr Leu Thr Glu Lys Lys Tyr Ser Ser Cys Ala Trp Glu Val Val
    130                 135                 140

nns nns gaa atc nns nns tcc ttc tct tta tca atc aac ttg caa aaa      480
Xaa Xaa Glu Ile Xaa Xaa Ser Phe Ser Leu Ser Ile Asn Leu Gln Lys
145                 150                 155                 160

aga ttg aag agt aag gaa                                              498
Arg Leu Lys Ser Lys Glu
                165


<210> SEQ ID NO 24
<211> LENGTH: 461
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Fusion Protein (IFNAR2 isoform 3 and Fc)

<400> SEQUENCE: 24

Ile Ser Tyr Asp Ser Pro Asp Tyr Thr Asp Glu Ser Cys Thr Phe Lys
1               5                   10                  15

Ile Ser Leu Arg Asn Phe Arg Ser Ile Leu Ser Trp Glu Leu Lys Asn
            20                  25                  30

His Ser Ile Val Pro Thr His Tyr Thr Leu Leu Tyr Thr Ile Met Ser
        35                  40                  45

Lys Pro Glu Asp Leu Lys Val Val Lys Asn Cys Ala Asn Thr Thr Arg
    50                  55                  60

Ser Phe Cys Asp Leu Thr Asp Glu Trp Arg Ser Thr His Glu Ala Tyr
65                  70                  75                  80

Val Thr Val Leu Glu Gly Phe Ser Gly Asn Thr Thr Leu Phe Ser Cys
                85                  90                  95

Ser His Asn Phe Trp Leu Ala Ile Asp Met Ser Phe Glu Pro Pro Glu
            100                 105                 110

Phe Glu Ile Val Gly Phe Thr Asn His Ile Asn Val Met Val Lys Phe
        115                 120                 125

Pro Ser Ile Val Glu Glu Glu Leu Gln Phe Asp Leu Ser Leu Val Ile
    130                 135                 140

Glu Glu Gln Ser Glu Gly Ile Val Lys Lys His Lys Pro Glu Ile Lys
145                 150                 155                 160

Gly Asn Met Ser Gly Asn Phe Thr Tyr Ile Ile Asp Lys Leu Ile Pro
                165                 170                 175
```

-continued

```
Asn Thr Asn Tyr Cys Val Ser Val Tyr Leu Glu His Ser Asp Glu Gln
            180                 185                 190

Ala Val Ile Lys Ser Pro Leu Lys Cys Thr Leu Leu Pro Pro Gly Gln
        195                 200                 205

Glu Ser Glu Phe Ser Ser Gly Arg Gly Gly Arg Arg Ala Ser Val Pro
    210                 215                 220

Asp Pro Glu Gly Glu Pro Lys Ser Cys Asp Lys Thr His Thr Cys Pro
225                 230                 235                 240

Pro Cys Pro Ala Pro Glu Leu Leu Gly Gly Pro Ser Val Phe Leu Phe
                245                 250                 255

Pro Pro Lys Pro Lys Asp Thr Leu Met Ile Ser Arg Thr Pro Glu Val
            260                 265                 270

Thr Cys Val Val Val Asp Val Ser His Glu Asp Pro Glu Val Lys Phe
        275                 280                 285

Asn Trp Tyr Val Asp Gly Val Glu Val His Asn Ala Lys Thr Lys Pro
    290                 295                 300

Arg Glu Glu Gln Tyr Asn Ser Thr Tyr Arg Val Val Ser Val Leu Thr
305                 310                 315                 320

Val Leu His Gln Asp Trp Leu Asn Gly Lys Glu Tyr Lys Cys Lys Val
                325                 330                 335

Ser Asn Lys Ala Leu Pro Ala Pro Ile Glu Lys Thr Ile Ser Lys Ala
            340                 345                 350

Lys Gly Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly Lys
    450                 455                 460
```

<210> SEQ ID NO 25
<211> LENGTH: 149
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (MUT2)
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t
<220> FEATURE:
<221> NAME/KEY: misc_feature
<222> LOCATION: (116)..(117)
<223> OTHER INFORMATION: n is a, c, g, or t

<400> SEQUENCE: 25

-continued

```
cagacatgac tttgaattcc cccaggagga gtttgatgat nnscagttcc agnnsgctca     60

agccatctct gtcctccatg agatgatcca gcagaccttc aacctcttca gcacannsga    120

ctcatctgct gctttggatg agacccttc                                      149
```

<210> SEQ ID NO 26
<211> LENGTH: 148
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (MUT2)
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (111)..(112)
<223> OTHER INFORMATION: n is a, c, g, or t

<400> SEQUENCE: 26

```
gcaagttgat tgataaagag aaggatctgt agatttccga gatgacaacc tcccaggcac     60

aagagctgta snnsnnctct gtcagatata gagtgattct ttggaagtas nncctcacag    120

ccaggatgga gtcctcgtac atcagggg                                       148
```

<210> SEQ ID NO 27
<211> LENGTH: 150
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (MUT2)
<220> FEATURE:
<221> NAME/KEY: misc_feature
<222> LOCATION: (108)..(109)
<223> OTHER INFORMATION: n is a, c, g, or t

<400> SEQUENCE: 27

```
cccagccggc catggcctgt gatctgcctc agactcacag cctgggtaac aggagggcct     60

tgatactcct ggcacaaatg cgaagaatct ctcctttctc ctgcctgnns gacagacatg    120

actttgaatt cccccaggag gagtttgatg                                     150
```

<210> SEQ ID NO 28
<211> LENGTH: 100
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (MUT2)
<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (49)..(50)
<223> OTHER INFORMATION: n is a, c, g, or t -continued

```
<220> FEATURE:
<221> NAME/KEY: misc_feature
<222> LOCATION: (58)..(59)
<223> OTHER INFORMATION: n is a, c, g, or t

<400> SEQUENCE: 28

ggcaccggcg cacctgcggc cgcagatcca ccaccacctt csnnactsnn caatctsnnt     60

tgcaagttga ttgataaaga gaaggatctg tagatttccg                          100


<210> SEQ ID NO 29
<211> LENGTH: 498
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Lysine-Replaced MUT2 (Library)
<220> FEATURE:
<221> NAME/KEY: mat_peptide
<222> LOCATION: (1)..(498)
<220> FEATURE:
<221> NAME/KEY: CDS
<222> LOCATION: (1)..(498)
<220> FEATURE:
<221> NAME/KEY: misc_feature
<222> LOCATION: (91)..(92)
<223> OTHER INFORMATION: n is a, c, g, or t
<220> FEATURE:
<221> NAME/KEY: misc_feature
<222> LOCATION: (136)..(137)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t
<220> FEATURE:
<221> NAME/KEY: misc_feature
<222> LOCATION: (211)..(212)
<223> OTHER INFORMATION: n is a, c, g, or t
<220> FEATURE:
<221> NAME/KEY: misc_feature
<222> LOCATION: (364)..(365)
<223> OTHER INFORMATION: n is a, c, g, or t
<220> FEATURE:
<221> NAME/KEY: misc_feature
<222> LOCATION: (400)..(401)
<223> OTHER INFORMATION: n is a, c, g, or t
<220> FEATURE:
<221> NAME/KEY: misc_feature
<222> LOCATION: (403)..(404)
<223> OTHER INFORMATION: n is a, c, g, or t
<220> FEATURE:
<221> NAME/KEY: misc_feature
<222> LOCATION: (478)..(479)
<223> OTHER INFORMATION: n is a, c, g, or t
<220> FEATURE:
<221> NAME/KEY: misc_feature
<222> LOCATION: (487)..(488)
<223> OTHER INFORMATION: n is a, c, g, or t
<220> FEATURE:
<221> NAME/KEY: misc_feature
<222> LOCATION: (493)..(494)
<223> OTHER INFORMATION: n is a, c, g, or t
<220> FEATURE:
<221> NAME/KEY: misc_feature
<222> LOCATION: (31)..(31)
<223> OTHER INFORMATION: The 'Xaa' at location 31 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (46)..(46)
<223> OTHER INFORMATION: The 'Xaa' at location 46 stands for Lys, Asn,
      Arg, Ser, Thr, Met, Ile, Glu, Asp, Gly, Ala, Val, Gln, His, Pro,
      Leu, Tyr, Trp, Cys, or Phe.
```

-continued

```
<220> FEATURE:
<221> NAME/KEY: misc_feature
<222> LOCATION: (50)..(50)
<223> OTHER INFORMATION: The 'Xaa' at location 50 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (71)..(71)
<223> OTHER INFORMATION: The 'Xaa' at location 71 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (122)..(122)
<223> OTHER INFORMATION: The 'Xaa' at location 122 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (134)..(134)
<223> OTHER INFORMATION: The 'Xaa' at location 134 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (135)..(135)
<223> OTHER INFORMATION: The 'Xaa' at location 135 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (160)..(160)
<223> OTHER INFORMATION: The 'Xaa' at location 160 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (163)..(163)
<223> OTHER INFORMATION: The 'Xaa' at location 163 stands for Lys, Asn,
      Arg, Ser, Thr, Met, Ile, Glu, Asp, Gly, Ala, Val, Gln, His, Pro,
      Leu, Tyr, Trp, Cys, or Phe.
<220> FEATURE:
<221> NAME/KEY: misc_feature
<222> LOCATION: (165)..(165)
<223> OTHER INFORMATION: The 'Xaa' at location 165 stands for Lys, Asn,
      Arg, Ser, Thr, Met, Ile, Glu, Asp, Gly, Ala, Val, Gln, His, Pro,
      Leu, Tyr, Trp, Cys, or Phe.

<400> SEQUENCE: 29

tgt gat ctg cct cag act cac agc ctg ggt aac agg agg gcc ttg ata       48
Cys Asp Leu Pro Gln Thr His Ser Leu Gly Asn Arg Arg Ala Leu Ile
1               5                   10                  15

ctc ctg gca caa atg cga aga atc tct cct ttc tcc tgc ctg nns gac       96
Leu Leu Ala Gln Met Arg Arg Ile Ser Pro Phe Ser Cys Leu Xaa Asp
            20                  25                  30

aga cat gac ttt gaa ttc ccc cag gag gag ttt gat gat nns cag ttc      144
Arg His Asp Phe Glu Phe Pro Gln Glu Glu Phe Asp Asp Xaa Gln Phe
        35                  40                  45

cag nns gct caa gcc atc tct gtc ctc cat gag atg atc cag cag acc      192
Gln Xaa Ala Gln Ala Ile Ser Val Leu His Glu Met Ile Gln Gln Thr
    50                  55                  60

ttc aac ctc ttc agc aca nns gac tca tct gct gct ttg gat gag acc      240
Phe Asn Leu Phe Ser Thr Xaa Asp Ser Ser Ala Ala Leu Asp Glu Thr
65                  70                  75                  80

ctt cta gat gaa ttc tac atc gaa ctt gac cag cag ctg aat gac ctg      288
Leu Leu Asp Glu Phe Tyr Ile Glu Leu Asp Gln Gln Leu Asn Asp Leu
                85                  90                  95

gag tcc tgt gtg atg cag gaa gtg ggg gtg ata gag tct ccc ctg atg      336
Glu Ser Cys Val Met Gln Glu Val Gly Val Ile Glu Ser Pro Leu Met
            100                 105                 110
```

-continued

```
tac gag gac tcc atc ctg gct gtg agg nns tac ttc caa aga atc act      384
Tyr Glu Asp Ser Ile Leu Ala Val Arg Xaa Tyr Phe Gln Arg Ile Thr
        115                 120                 125

cta tat ctg aca gag nns nns tac agc tct tgt gcc tgg gag gtt gtc      432
Leu Tyr Leu Thr Glu Xaa Xaa Tyr Ser Ser Cys Ala Trp Glu Val Val
    130                 135                 140

atc tcg gaa atc tac aga tcc ttc tct tta tca atc aac ttg caa nns      480
Ile Ser Glu Ile Tyr Arg Ser Phe Ser Leu Ser Ile Asn Leu Gln Xaa
145                 150                 155                 160

aga ttg nns agt nns gaa                                              498
Arg Leu Xaa Ser Xaa Glu
                165


<210> SEQ ID NO 30
<211> LENGTH: 27
<212> TYPE: DNA
<213> ORGANISM: Artificial Sequence
<220> FEATURE:
<223> OTHER INFORMATION: Synthetic

<400> SEQUENCE: 30

tctcctaggt cattcgggac tgagcaa                                         27


<210> SEQ ID NO 31
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: PCR primer (MUT2K134)

<400> SEQUENCE: 31

tctcctaggt cattccgtac tggccaa                                         27
```